(12) United States Patent
Abu Qudeiri et al.

(10) Patent No.: US 11,672,666 B1
(45) Date of Patent: Jun. 13, 2023

(54) HIP IMPLANT WITH REDUCED WEAR

(71) Applicant: United Arab Emirates University, Al Ain (AE)

(72) Inventors: Jaber Abu Qudeiri, Al Ain (AE); Asarudheen Abdudeen, Al Ain (AE); Mini Rema Sahadevan, Thiruvananthapuram (IN); Anantha Padmanabhan M, Thiruvananthapuram (IN)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/824,535

(22) Filed: May 25, 2022

(51) Int. Cl.
    *A61F 2/36*      (2006.01)
    *A61F 2/34*      (2006.01)
    *A61F 2/30*      (2006.01)

(52) U.S. Cl.
    CPC .............. *A61F 2/3609* (2013.01); *A61F 2/34* (2013.01); *A61F 2/3662* (2013.01); *A61F 2002/30113* (2013.01); *A61F 2002/30154* (2013.01); *A61F 2002/30807* (2013.01); *A61F 2002/30828* (2013.01); *A61F 2002/3611* (2013.01)

(58) Field of Classification Search
    CPC ......... A61F 2/3609; A61F 2/34; A61F 2/3662
See application file for complete search history.

(56) References Cited

U.S. PATENT DOCUMENTS 5,879,406 A * 3/1999 Lilley ................ A61F 2/32
                                                         623/22.15
2002/0116068 A1 * 8/2002 McLean .............. A61F 2/32
                                                         623/22.15

FOREIGN PATENT DOCUMENTS

WO    WO-2013086150 A1 * 6/2013 ........... A61F 2/3886

OTHER PUBLICATIONS

Schmidig et al., The Effects of Acetabular Shell Deformation and Liner Thickness on Frictional Torque in UHMW Polyethelene Acetabular Bearings, The Journal of Arthroplasty, vol. 25 No. 4, pp. 644-653. (Year: 2010).*

* cited by examiner

*Primary Examiner* — Brian A Dukert
(74) *Attorney, Agent, or Firm* — Hayes Soloway PC

(57) ABSTRACT

There is disclosed a hip implantation structure, comprising a stem and a femoral head, the femoral head comprising a plurality of grooves, an outer acetabular cup and an inner liner, wherein presence of the inner liner and plurality of grooves on the femoral head reduces friction and thereby reduces wear of the hip implantation structure. The hip implantation structure is used for total hip arthroplasty. The plurality of grooves on the femoral head comprises a plurality of hemispherical grooves of varying widths, and debris produced by the inner liner gets trapped inside the plurality of grooves, resulting in a reduced chance of adhesive wear.

13 Claims, 14 Drawing Sheets

| Load (N) | 600 | 650 | 700 | 750 | 800 | 850 |
|---|---|---|---|---|---|---|
| Contact pressure (MPa) | Pressure<br>Type: Pressure<br>Unit: Pa<br>Time: 1<br>16-06-2021 23:42<br>1.8626e6 Max<br>1.6556e6<br>1.4487e6<br>1.2417e6<br>1.0348e6<br>8.2781e5<br>6.2086e5<br>4.1391e5<br>4.0695e5<br>0 Min | Pressure<br>Type: Pressure<br>Unit: Pa<br>Time: 1<br>16-06-2021 23:48<br>1.9262e6 Max<br>1.7121e6<br>1.4981e6<br>1.2841e6<br>1.0701e6<br>8.5607e5<br>6.4206e5<br>4.2804e5<br>2.1402e5<br>0 Min | Pressure<br>Type: Pressure<br>Unit: Pa<br>Time: 1<br>16-06-2021 23:53<br>1.9882e6 Max<br>1.7673e6<br>1.5464e6<br>1.3254e6<br>1.1045e6<br>8.8363e5<br>6.6272e5<br>4.4182e5<br>2.2091e5<br>0 Min | Pressure<br>Type: Pressure<br>Unit: Pa<br>Time: 1<br>16-06-2021 23:56<br>2.0496e6 Max<br>1.8291e6<br>1.5942e6<br>1.3664e6<br>1.1387e6<br>9.1095e5<br>6.8321e5<br>4.5547e5<br>2.2774e5<br>0 Min | Pressure<br>Type: Pressure<br>Unit: Pa<br>Time: 1<br>16-06-2021 00:00<br>2.1102e6 Max<br>1.8757e6<br>1.6413e6<br>1.4068e6<br>1.1723e6<br>9.3787e5<br>7.034e5<br>4.6894e5<br>2.3447e5<br>0 Min | Pressure<br>Type: Pressure<br>Unit: Pa<br>Time: 1<br>16-06-2021 00:03<br>2.1696e6 Max<br>1.9286e6<br>1.6875e6<br>1.4464e6<br>1.2053e6<br>9.6428e5<br>7.2321e5<br>4.8214e5<br>2.4107e5<br>0 Min |
| Sliding distance (mm) | Sliding Distance<br>Type: Sliding Distance<br>Unit: m<br>Time: 1<br>16-06-2021 23:44<br>1.8793e-5 Max<br>1.6705e-5<br>1.4617e-5<br>1.2529e-5<br>1.044e-5<br>8.3523e-6<br>6.2643e-6<br>4.1762e-6<br>2.0881e-6<br>0 Min | Sliding Distance<br>Type: Sliding Distance<br>Unit: m<br>Time: 1<br>16-06-2021 23:48<br>2.0257e-5 Max<br>1.8006e-5<br>1.5755e-5<br>1.3505e-5<br>1.1254e-5<br>9.0031e-6<br>6.7523e-6<br>4.5016e-6<br>2.2508e-6<br>0 Min | Sliding Distance<br>Type: Sliding Distance<br>Unit: m<br>Time: 1<br>16-06-2021 23:53<br>2.1701e-5 Max<br>1.929e-5<br>1.6879e-5<br>1.4468e-5<br>1.2056e-5<br>9.645e-6<br>7.2338e-6<br>4.8225e-6<br>2.4113e-6<br>0 Min | Sliding Distance<br>Type: Sliding Distance<br>Unit: m<br>Time: 1<br>16-06-2021 23:57<br>2.3128e-5 Max<br>2.0558e-5<br>1.7988e-5<br>1.5419e-5<br>1.2849e-5<br>1.0279e-5<br>7.7093e-6<br>5.1395e-6<br>2.5698e-6<br>0 Min | Sliding Distance<br>Type: Sliding Distance<br>Unit: m<br>Time: 1<br>17-06-2021 00:00<br>2.4534e-5 Max<br>2.1808e-5<br>1.9082e-5<br>1.6356e-5<br>1.363e-5<br>1.0904e-5<br>8.178e-6<br>5.452e-6<br>2.726e-6<br>0 Min | Sliding Distance<br>Type: Sliding Distance<br>Unit: m<br>Time: 1<br>17-06-2021 00:04<br>2.5917e-5 Max<br>2.3037e-5<br>2.0158e-5<br>1.7278e-5<br>1.4398e-5<br>1.1519e-5<br>8.639e-6<br>5.7593e-6<br>2.8797e-6<br>0 Min |

FIG. 9

| Load (N) | 600 | 650 | 700 | 750 | 800 | 850 |
|---|---|---|---|---|---|---|
| Contact pressure (MPa) | A: 1 mm liner<br>Pressure<br>Type: Pressure<br>Unit: Pa<br>Time:1<br>19-06-2021 22:32<br><br>1.5125e6 Max<br>1.3473e6<br>1.182e6<br>1.0167e6<br>8.5145e5<br>6.8618e5<br>5.2091e5<br>3.5564e5<br>1.9037e5<br>25101 Min | A: 1 mm liner<br>Pressure<br>Type: Pressure<br>Unit: Pa<br>Time:1<br>19-06-2021 22:35<br><br>1.5932e6 Max<br>1.4193e6<br>1.2455e6<br>1.0716e6<br>8.9777e5<br>7.2392e5<br>5.5006e5<br>3.7621e5<br>2.0236e5<br>28510 Min | A: 1 mm liner<br>Pressure<br>Type: Pressure<br>Unit: Pa<br>Time:1<br>19-06-2021 22:37<br><br>1.6751e6 Max<br>1.4925e6<br>1.3099e6<br>1.1274e6<br>9.4479e5<br>7.6222e5<br>5.7965e5<br>3.9709e5<br>2.1452e5<br>31949 Min | A: 1 mm liner<br>Pressure<br>Type: Pressure<br>Unit: Pa<br>Time:1<br>19-06-2021 22:39<br><br>1.7568e6 Max<br>1.5655e6<br>1.3741e6<br>1.1828e6<br>9.9148e5<br>8.0015e5<br>6.0883e5<br>4.175e5<br>2.2617e5<br>34849 Min | A: 1 mm liner<br>Pressure<br>Type: Pressure<br>Unit: Pa<br>Time:1<br>19-06-2021 22:42<br><br>1.8397e6 Max<br>1.6393e6<br>1.4388e6<br>1.2384e6<br>1.038e6<br>8.3759e5<br>6.3718e5<br>4.3676e5<br>2.3635e5<br>35935 Min | A: 1 mm liner<br>Pressure<br>Type: Pressure<br>Unit: Pa<br>Time:1<br>19-06-2021 22:45<br><br>1.9229e6 Max<br>1.7134e6<br>1.5038e6<br>1.2943e6<br>1.0847e6<br>8.7513e5<br>6.6556e5<br>4.56e5<br>2.4644e5<br>36874 Min |
| Sliding distance (mm) | A: 1 mm liner<br>Sliding Distance<br>Type: Sliding Distance<br>Unit: m<br>Time:1<br>19-06-2021 22:34<br><br>2.5389e-5 Max<br>2.2571e-5<br>1.9753e-5<br>1.6935e-5<br>1.4117e-5<br>1.1299e-5<br>8.4813e-6<br>5.6635e-6<br>2.8456e-6<br>2.7694e-8 Min | A: 1 mm liner<br>Sliding Distance<br>Type: Sliding Distance<br>Unit: m<br>Time:1<br>19-06-2021 22:36<br><br>2.7407e-5 Max<br>2.4365e-5<br>2.1323e-5<br>1.8281e-5<br>1.5239e-5<br>1.2196e-5<br>9.1542e-6<br>6.112e-6<br>3.0699e-6<br>2.7672e-8 Min | A: 1 mm liner<br>Sliding Distance<br>Type: Sliding Distance<br>Unit: m<br>Time:1<br>19-06-2021 22:38<br><br>2.9413e-5 Max<br>2.6148e-5<br>2.2883e-5<br>1.9618e-5<br>1.6353e-5<br>1.3088e-5<br>9.8233e-6<br>6.5583e-6<br>3.2933e-6<br>2.8292e-8 Min | A: 1 mm liner<br>Sliding Distance<br>Type: Sliding Distance<br>Unit: m<br>Time:1<br>19-06-2021 22:40<br><br>3.1411e-5 Max<br>2.7924e-5<br>2.4438e-5<br>2.0951e-5<br>1.7464e-5<br>1.3977e-5<br>1.049e-5<br>7.0031e-6<br>3.5162e-6<br>2.9342e-8 Min | A: 1 mm liner<br>Sliding Distance<br>Type: Sliding Distance<br>Unit: m<br>Time:1<br>19-06-2021 22:43<br><br>3.3384e-5 Max<br>2.9678e-5<br>2.5972e-5<br>2.2266e-5<br>1.856e-5<br>1.4854e-5<br>1.1148e-5<br>7.4425e-6<br>3.7366e-6<br>3.067e-8 Min | A: 1 mm liner<br>Sliding Distance<br>Type: Sliding Distance<br>Unit: m<br>Time:1<br>19-06-2021 22:45<br><br>3.5331e-5 Max<br>3.1408e-5<br>2.7486e-5<br>2.3564e-5<br>1.9642e-5<br>1.572e-5<br>1.1798e-5<br>7.8761e-6<br>3.954e-6<br>3.1922e-8 Min |

HIP IMPLANT WITH REDUCED WEAR

FIELD OF THE INVENTION

The present invention relates to the field of hip arthroplasty, and more particularly to a hip implant with reduced wear properties.

BACKGROUND OF THE INVENTION

Background description includes information that will be useful in understanding the present invention. It is not an admission that any of the information provided herein is prior art or relevant to the presently claimed invention, or that any publication specifically or implicitly referenced is prior art.

Hip arthroplasty/replacement is a surgical procedure in which the hip joint is replaced by a prosthetic implant, that is, a hip prosthesis. Hip replacement surgery can be performed as a total replacement or a hemi replacement.

The most common type of hip replacement surgery is called a total hip replacement (also called total hip arthroplasty). In this surgery, worn-out or damaged sections of the hip are replaced with artificial implants. In total hip replacement (also called total hip arthroplasty), the damaged bone and cartilage is removed and replaced with prosthetic components. Total hip replacement is a highly effective surgical procedure for patients suffering from end stage osteoarthritis and its success in improving symptoms of osteoarthritis has meant that its use has increased across many healthcare systems. Although in experienced hands the procedure provides very effective outcomes, one must be aware of the potential complications of the procedure.

Hip replacement complications include blood clots, change in leg length, dislocation, fractures, infection and loosening of the implant. People who have received metal-on-metal hips may also experience metallosis, a form of metal poisoning that causes tissue damage and other serious conditions. However, wear is one of the major problems existing in total hip arthroplasty. Wear results when surfaces produce local mechanical damage and unwanted loss of material and the resultant generation of wear particles. The most common cause of a hip replacement wearing out is called aseptic loosening. Aseptic loosening occurs when the hip implants become loose within the bone, and a loose hip implant tends to be painful and usually requires revision hip replacement. Many researches have been conducted and are yet ongoing to minimize the problem using different numerical and experimental methods.

Accordingly, there exists a need for a solution, which overcomes the drawbacks faced by traditionally employed hip arthroplasty implants.

SUMMARY OF THE INVENTION

Therefore, it is an object of the present invention to develop a hip implant with reduced wear properties, which overcomes the drawbacks faced by traditionally employed hip arthroplasty prosthetics or implants.

The disclosed is a hip implantation structure, comprising a stem and a femoral head, the femoral head comprising a plurality of grooves, an outer acetabular cup and an inner liner, wherein presence of the inner liner and plurality of grooves on the femoral head reduces friction and thereby resulting wear of the hip implant structure.

In an embodiment of the present invention, the hip implantation structure is used for total hip arthroplasty.

In another embodiment of the present invention, the outer acetabular cup and liner are inserted into a medullary canal of a femur bone.

In another embodiment of the present invention, the femoral head is hemi-spherical in structure.

In another embodiment of the present invention, the femoral head is made of titanium alloy (Ti6Al4V) and the inner liner is made of ultra-high molecular weight poly ethylene (UHMWPE).

In another embodiment of the present invention, an inner radius of the inner liner is 16 mm and an outer radius of the inner liner is 23 mm.

In another embodiment of the present invention, an additional or second liner is further placed between the femoral head and the inner liner, wherein the additional or second liner is made of UHMWPE.

In another embodiment of the present invention, a thickness of the additional or second liner is 1 mm, 2 mm or 3 mm.

In another embodiment of the present invention, the plurality of grooves on the femoral head comprises a plurality of hemispherical grooves of varying widths.

In another embodiment of the present invention, debris produced by the inner liner gets trapped inside the plurality of grooves, resulting in a reduced chance of adhesive wear.

In another embodiment of the present invention, a surface of the femoral head is textured.

In another embodiment of the present invention, the surface of the femoral head comprises a plurality of circular and square shaped dimples.

In another embodiment of the present invention, an edge length of the circular dimples is of 2 mm and an edge length of the square dimples is 1.57 mm.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

FIG. 9 shows the maximum values of contact stress and sliding distance obtained for the femoral head with 1 mm wide groove under different body weights.

FIG. 11 shows the maximum values of contact stress and sliding distance obtained for femoral head with additional liner of 1 mm thickness.

DETAILED DESCRIPTION OF THE INVENTION

The aspects of the proposed hip implant with reduced wear properties, according to the present invention will be described in conjunction with FIGS. 1-14. In the detailed description, reference is made to the accompanying figures, which form a part hereof, and which is shown by way of illustration of specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The hip joint is a ball-and-socket synovial joint in the pelvis that connects the acetabulum and femur, which can transmit both static & dynamic loads with ease. It can transfer large dynamic loads (7-8 times the body weight) and can handle a wide variety of motions. The hip joint is one of the essential joints which enables us to stand, walk, run, leap, sit, climb stairs and bend. Hip replacement surgery, also known as total hip arthroplasty (THA), involves replacing a damaged or injured hip joint with an artificial joint or implant. Hip replacements are often done when arthritis cause significant hip pain and inflammation, and is also performed for a variety of causes, including hip fractures and natural wear and tear. The method of surgery, design of implant, stem arrangement, the stability of fixation, weight of the patient and roughness of implant are some of the factors influencing the long-term survival of the prosthetic hip joint.

Figure 1:
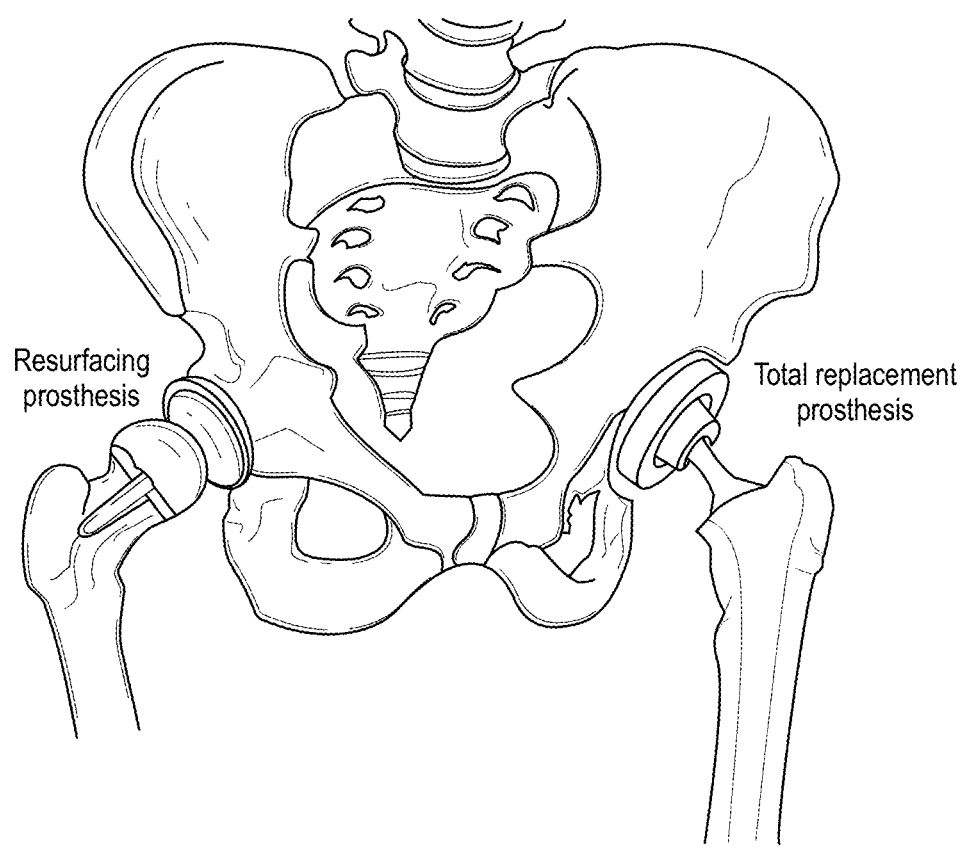
FIG. 1 is a perspective view of an artificial hip joint by total hip replacement (THR) or by partial hip replacement or hip resurfacing.

An artificial hip joint or hip implant can replace a damaged hip joint in two ways, either by total hip replacement (THR) or by partial hip replacement or hip resurfacing as shown in FIG. 1. In total hip replacement, the implant which consists of stem, femoral head, acetabular cup and liner, is inserted into the medullary canal of femur bone with or without cement material and acetabular cup fits into the acetabulum. In hip resurfacing, only the acetabular cup and femoral head are involved. An implant placed in touch with a bone, fuses with it gradually and this process is known as osseointegration.

Different types of biomaterials are used in hip implants, which includes metals, polymers, ceramics etc. Metal-on-Polyethylene (MoP), Metal-on-Metal (MoM), Ceramic-on-Ceramic (CoC), Ceramic-on-Polyethylene (COPE) are the common material combinations used in femoral head. Titanium alloys, and cobalt-chromium alloys are the commonly used materials for femoral head. Structural and microstructural studies of titanium alloys, used in orthopedic implants, are performed to guarantee its safe and successful usage. The release of metal ions from titanium implants, into the cells near the bone even in tiny levels can cause discomfort to the tissues around the implants. In this regard, placing an additional liner may reduce the wear rate and further release of metal ions. The magnitude of load and the way in which it is carried out may also have an impact on the stresses developed in hip joints. Many numerical models have been developed to study the hip joint, for example, hip joint wear and the resulting temperature developed in the surrounding zone are numerically determined using finite element method. Also, von Mises stress and displacement in circular, elliptical, oval and trapezoidal stems are determined using finite element method. Furthermore, the wear and fatigue characteristics at the head-stem interface of hip implant made with Co—Cr—Mo-Alumina, Ti6Al4V-Alumina, and CoCrMo—Ti6Al4V combinations have been numerically analyzed traditionally. The fatigue behaviour was investigated with the help of Goodman's mean stress fatigue theory, whereas modified Archard's wear model was adopted to examine the wear rate. Many other studies have also discussed the deformation and von Mises stresses developed in hip implants. Deformation and von Mises stresses are observed to be minimum for hip implant with trapezoidal stem of Cobalt chromium and acetabular cup of CoC. Also, it has been observed that there is a reduction in von Mises stresses when femoral head size is increased and neck length is reduced. Further, optimized cross section of trapezoidal shaped hip implant have been determined using Design of Experiment (DoE) through ANSYS R-19.

Hip prosthesis are of two types, unipolar and bipolar. A stem, a femoral head, a liner, and an outer cup are included in the unipolar model, while a bipolar model constitutes a stem, a femoral head, an inner liner, an outer liner and an outer cup. A plastic material is placed as a liner in between the femoral head and outer cup since attaching plastic to metal is advantageous as it reduces tensile stresses at the edge of the contact zone and octahedral and maximum shear stresses directly beneath the load. It also reduces friction and the resulting wear. Textured surfaces are frequently used on a wide range of mechanical components, and total hip arthroplasty with implants containing textured surface can minimize surface contact area, adhesive wear, and coefficient of friction. Several studies have also demonstrated that surface texturing on contact surfaces improved tribological performance. The existing hip implant model including a femoral head, stem, liner, and backing material still faces issues with respect to osseointegration. Moreover, unstable fracture development, fatigue failures and inflammation in the presence of wear debris have been reported while using the available designs and material combinations. Previous studies also propose some surface and design modifications on the model to reduce the area of contact and the resulting contact stress and wear debris. Different design and surface modifications are incorporated on the traditionally implemented hip implant model by introducing some new features like hemispherical grooves of different width on the femoral head and by providing an additional inner liner of ultra-high molecular weight poly ethylene (UHMWPE) between the femoral head and liner to prevent direct contact of metallic surface and plastic material. Moreover, a comparative analysis in the presence of circular and square dimples on the femoral head surface has also been conducted. For these study-related purposes, the wear volume is calculated using Archard's wear equation, and contact pressure and sliding distance values are obtained from ANSYS finite element method.

A major issue faced by modern hip arthroplasty is wear in the articulating surface and wear induced debris. Thus, the proposed design of hip implant is highly important for its longevity. Experimental demonstration of wear in hip implant involves both time and cost. In this regard, finite element analysis acts as a suitable alternative. In the present invention, the wear characteristics of design and surface modified femoral head are studied. Femoral head is assumed to be made of Ti6Al4V and liner material is taken as UHMWPE. The study conducted involves development of a new femoral head and its simulation using ANSYS under static load condition to get the contact pressure and sliding distance. Modified Archard's wear equation uses contact stress and sliding distance to determine the wear volume produced per year and the obtained results are compared with the traditionally implemented implants/available literature. The conducted study shows that the wear rate is reduced up to 10% by surface modification and 3% by design modifications.

In general, femoral head surface of the hip implant is smooth in nature with four parts such as stem, femoral head, liner and an outer cup. In an embodiment of the present invention, different design and surface modifications are incorporated on the existing hip implant model by introducing new features like hemispherical grooves of different width on the femoral head and by providing an additional inner liner of ultra-high molecular weight poly ethylene (UHMWPE) with different thickness between femoral head and liner to prevent direct contact of metallic surface and plastic material. Moreover, a comparative analysis in the presence of circular and square dimples on the femoral head surface is also conducted.

Common bio materials used to produce an implant are zirconia, zirconia toughened alumina (ZTA), Titanium alloys, stainless steel, special high-strength alloys, alumina, ultra-high molecular weight poly ethylene (UHMWPE), and Polytetrafluoroethylene (PTFE). Femoral heads are typically 28 mm (1.1 in), 32 mm (1.3 in) or 36 mm in size (1.4 in). The dimensions used for the construction of the hip implant model, in accordance with the present invention, are given in Table 1.

TABLE 1

Dimensions of implant head

| Parts | Inner Radius (mm) | Outer Radius (mm) |
| --- | --- | --- |
| Femoral head | 0 | 16 |
| Liner | 16 | 23 |
| Outer cup | 23 | 26 |

Figure 2A:
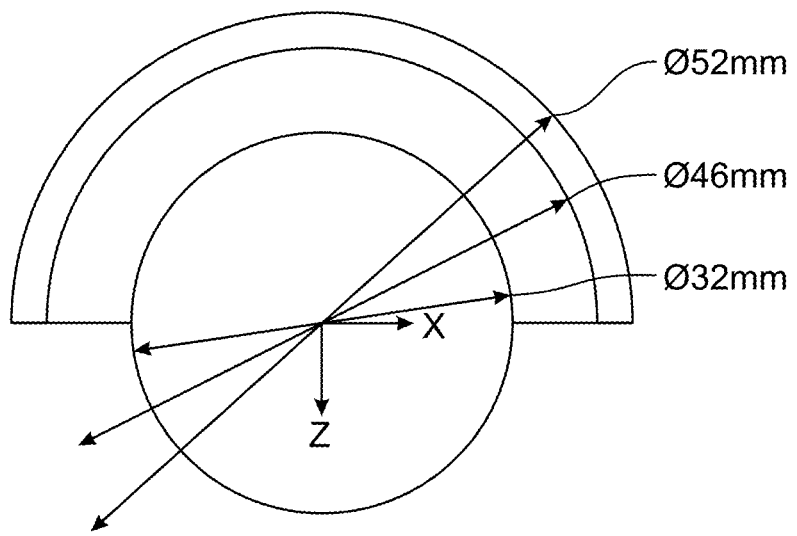
FIG. 2a and FIG. 2b depict numerical models of the femoral head region consisting of a femoral head of diameter 32 mm made with Ti6Al4V, UHMWPE liner of 7 mm thick and an outer acetabular cup made with same titanium alloy, respectively.
Figure 2B:
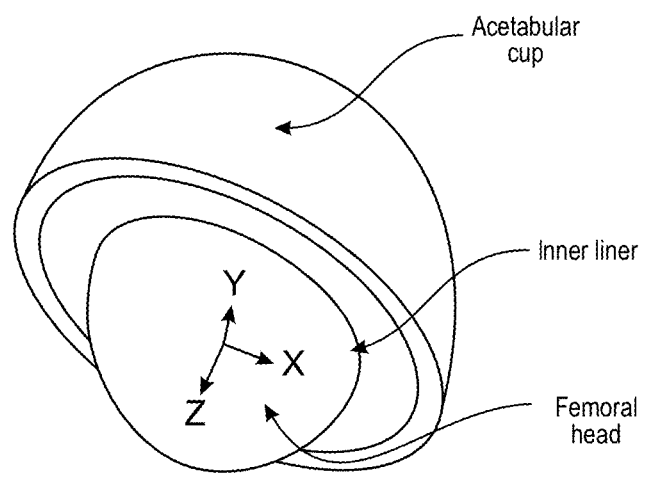

Titanium alloys (Ti6Al4V), stainless steel, and cobalt-chromium-molybdenum alloys are the commonly used metals and alloys for THA. In comparison to other metals, they have high corrosion resistance, wear resistance, greater toughness, and hardness than other metals and polymers. Polymer materials are the primary option for low friction hip replacements. Due to the outstanding mechanical characteristics and great wear resistance, polymers such as Polytetrafluoroethylene (PTFE), poly ether ether ketone (PEEK) have also started to be used. The material properties of Ti6Al4V and UHMWPE are given in Table 2, and a numerical model of the femoral head region consisting of a femoral head of diameter 32 mm made with Ti6Al4V, UHMWPE liner of 7 mm thick and an outer acetabular cup made with same titanium alloy is shown in FIG. 2a and FIG. 2b. The model is considered without any clearance between femoral head and liner and this model is finally simulated using ANSYS 20R1 workbench after applying all the boundary conditions.

TABLE 2

Properties of bio materials chosen

| Material | Density (g/cc) | Elastic Modules (GPa) | Poisson's Ratio |
| --- | --- | --- | --- |
| Ti6Al4V | 4.5 | 110 | 0.33 |
| UHMWPE | 0.95 | 0.725 | 0.45 |

The major parameters influencing the wear volume produced per year in a hip implant include contact pressure and sliding distance. Contact stress or contact pressure values are discontinuous at all times and the contact region changes in a significant way and as a result, finite element methods are used to tackle such problems in a model to properly quantify the wear volume. Moreover, computational methods help to minimize the number of expensive experiments. The contact status of two bodies under static conditions is expressed in the matrix form:

$$[K]\{q\}=\{F\}^{ext} \quad (1)$$

where $\{F\}^{ext}$ is the external force, [K] is the combined stiffness matrix and $\{q\}$ is the nodal displacement matrix. The contact pressure between these articulating surfaces is calculated using the above equation and the obtained contact stress and sliding distance are applied directly into modified Archard's wear law for calculating wear volume, for a constant value of wear coefficient. The wear volume is determined using modified Archard's wear law:

$$V=K_w \sigma_c A S_L \quad (2)$$

where, $K_w$ is the wear coefficient in mm³/Nm, $K_w=0.235 \times 10^{-4} \times R_a^{203}$, V is the wear volume in mm³, $R_a$ is the surface roughness, $S_L$ is the sliding distance in mm, $\sigma_c$ is the contact pressure in MPa and A is the contact area in mm².

Figure 3:
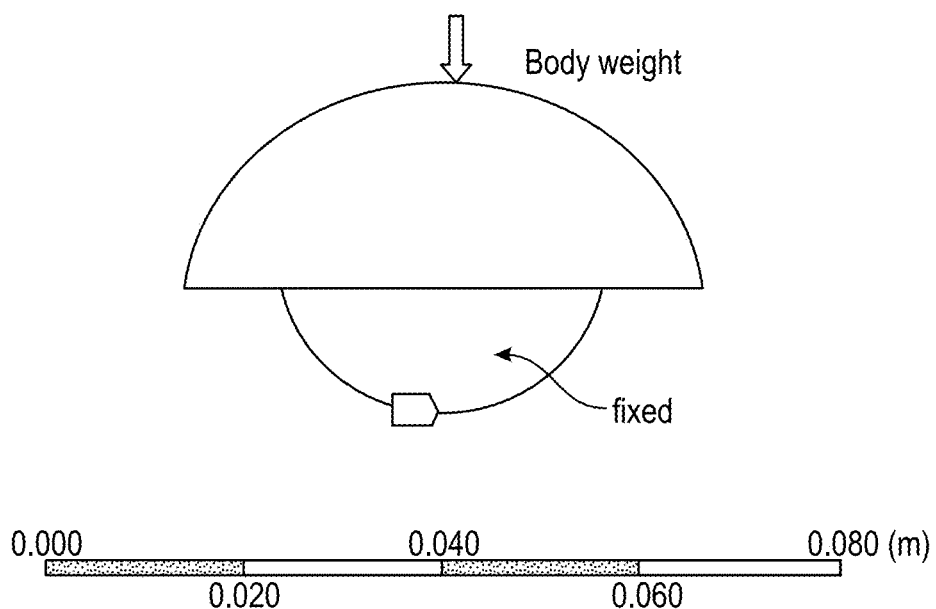
FIG. 3 shows the contact between the femoral head and liner, and the liner being fixed with the acetabular cup.

In accordance with the present invention, considering boundary conditions, finite element analysis of the femoral head of an artificial hip joint implant is performed with various body weights under static load condition. To ensure safety of the hip joint, the maximum weight applied to it in standing position is taken as 6 to 7 times the body weight. The contact behavior of hip joint parts is considered to be symmetric, and the contact algorithm used is the Augmented Lagrange technique. The load is applied on the top of acetabular cup surface in the Z direction by keeping the spherical femoral head in fixed manner. The contact between the femoral head and liner is frictional and the liner is fixed with the acetabular cup as shown in FIG. 3. Validation is done on the femoral head model shown in FIG. 3, by keeping the same boundary conditions and same loads. The material combination selected for the validation purpose is given in Table 3.

TABLE 3

Biomaterial combination used for validation of the numerical model

| Cases | Femoral head | Inner liner | Outer cup |
|---|---|---|---|
| Case 1 | Ti6Al4V | UHMWPE | Ti6Al4V |

Figure 4:
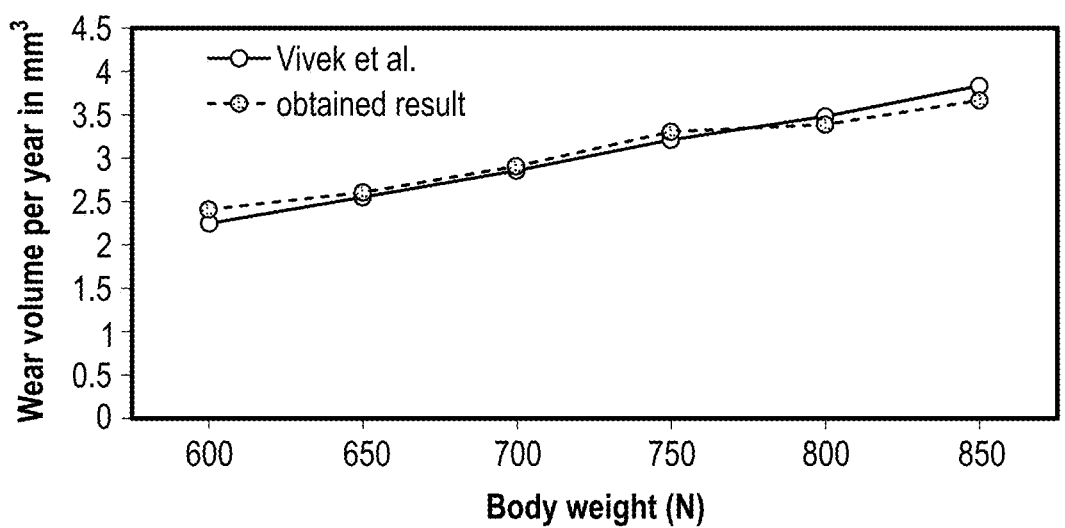
FIG. 4 shows a comparison graph between wear volume per year in mm$^3$ for different body weights with the results available via traditional methods/literature.

Different loads like 600 N, 650 N, 700 N, 750 N, 800 N and 850 N are applied on the top of the acetabular cup and contact pressure and sliding distance corresponding to each loading condition are extracted. The obtained values are used to determine the wear volume produced per year from Archard's wear law. Wear volume per year in $mm^3$ for different body weights are plotted and compared with the results available in literature is shown in FIG. 4.

Figure 5A:
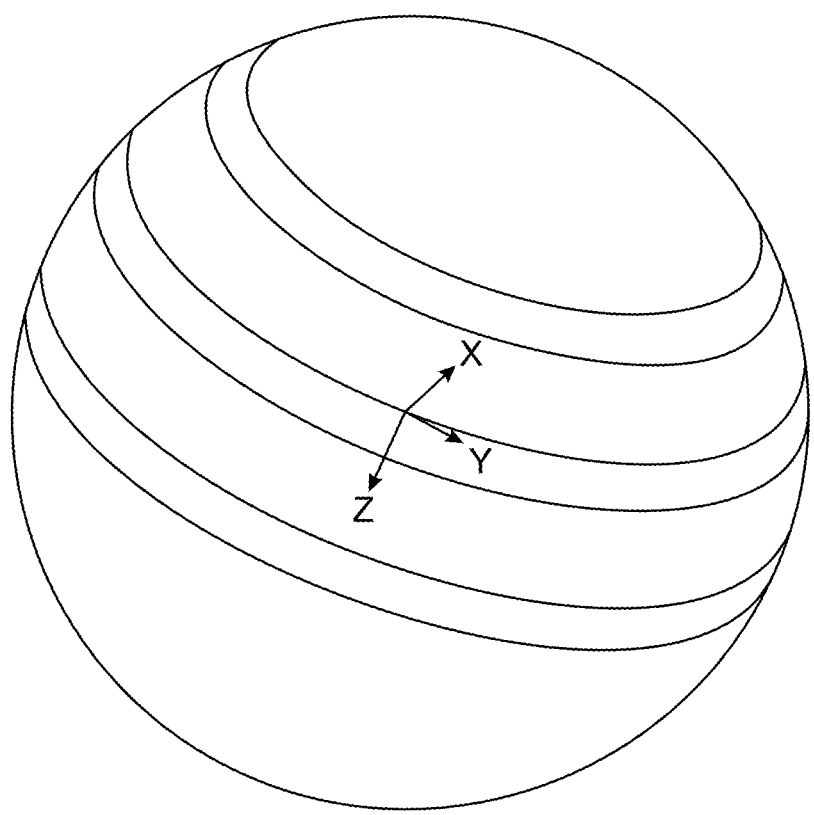
FIG. 5a shows semi-circular grooves of different widths like 1 mm, 2 mm, 3 mm and 4 mm provided on the femoral head surface to reduce the area of contact in such way that there is reduced chance of adhesive wear as the liner debris get trapped inside those grooves.
Figure 5B:
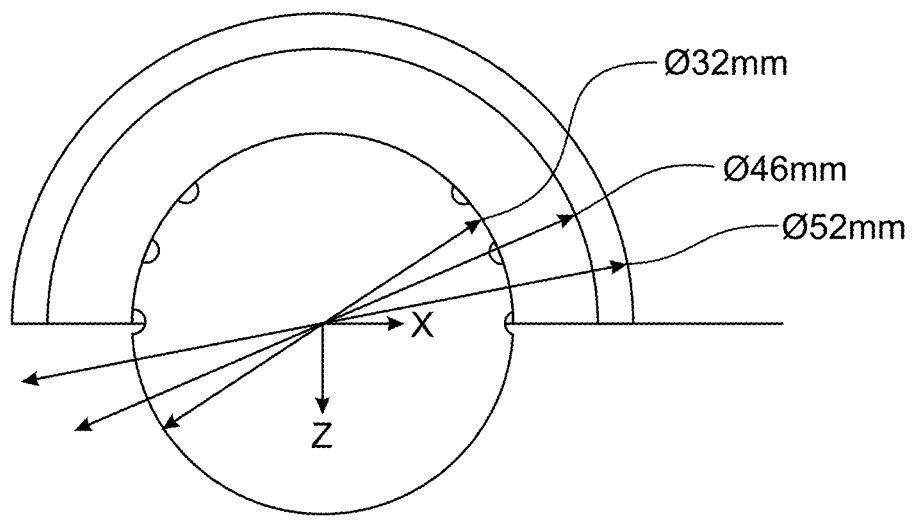
FIG. 5b depicts a cross sectional view showing femoral head with groove, liner and acetabular cup, in accordance with the present invention.

Considering a numerical analysis in accordance with the present invention, the femoral head surface needs to be studied in different ways to solve the existing issues associated with the hip implant. Since wear is one of the major factors that reduces the longevity of a hip implant, the area of contact between femoral head and the liner part of acetabular component requires special attention. In this context, numerical analysis of three different surface/design modifications were considered. Initially, surface modification of the femoral head is done by providing semicircular grooves. Semicircular grooves of different widths like 1 mm, 2 mm, 3 mm and 4 mm are provided on the femoral head surface, as shown in FIG. 5a, to reduce the area of contact in such way that there is reduced chance of adhesive wear as the liner debris get trapped inside those grooves. FIG. 5b depicts a cross sectional view showing femoral head with groove, liner and acetabular cup.

Figure 6A:
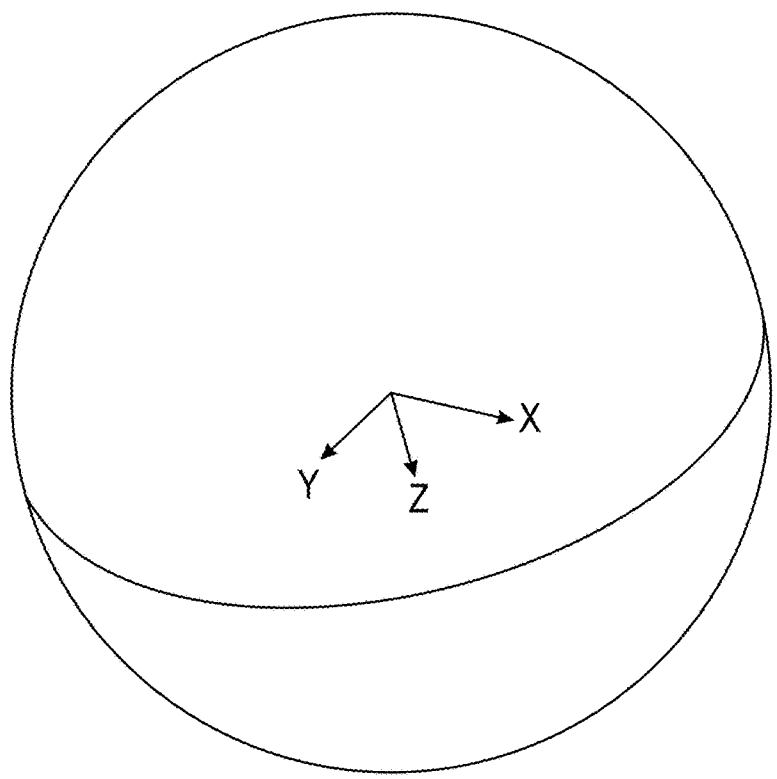
FIG. 6a shows metal on plastic type of contact between femoral head and liner being converted to plastic-on-plastic type of contact by attaching an additional liner material (UHMWPE) on the hemispherical surface of femoral head (Ti6Al4V).
Figure 6B:
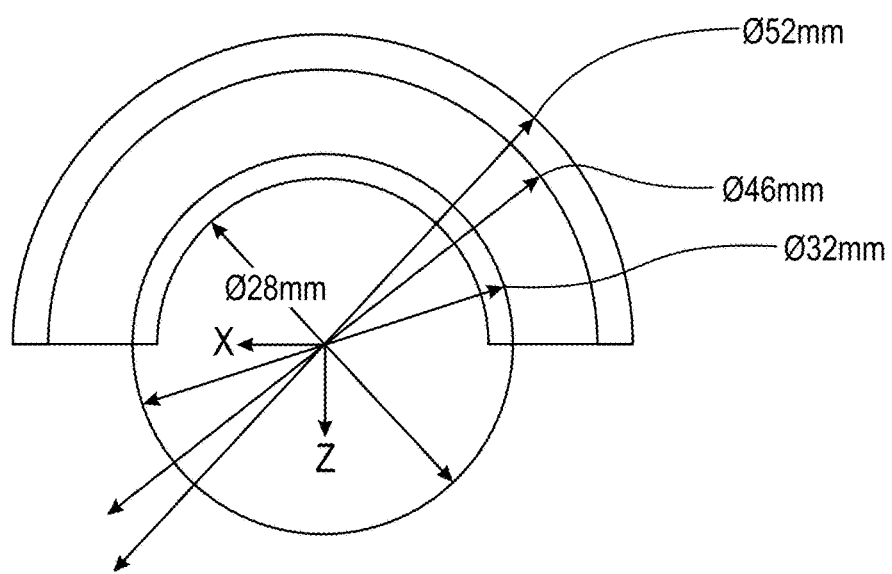
FIG. 6b depicts a cross sectional view of the femoral head provided with the additional liner, in accordance with the present invention.
Figure 7A:
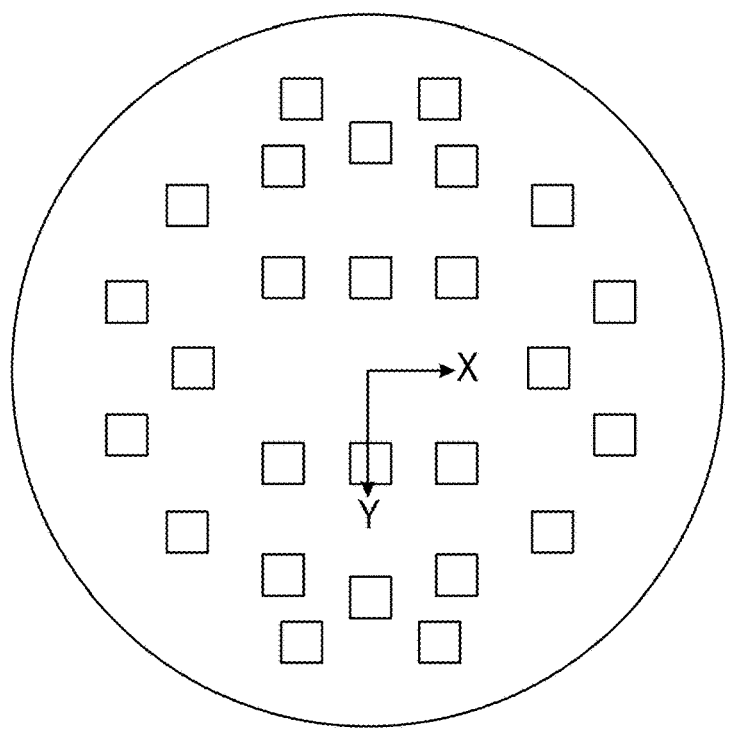
FIG. 7a and FIG. 7b show schematic diagrams of the textured surfaces considered in accordance with the present invention.
Figure 7B:
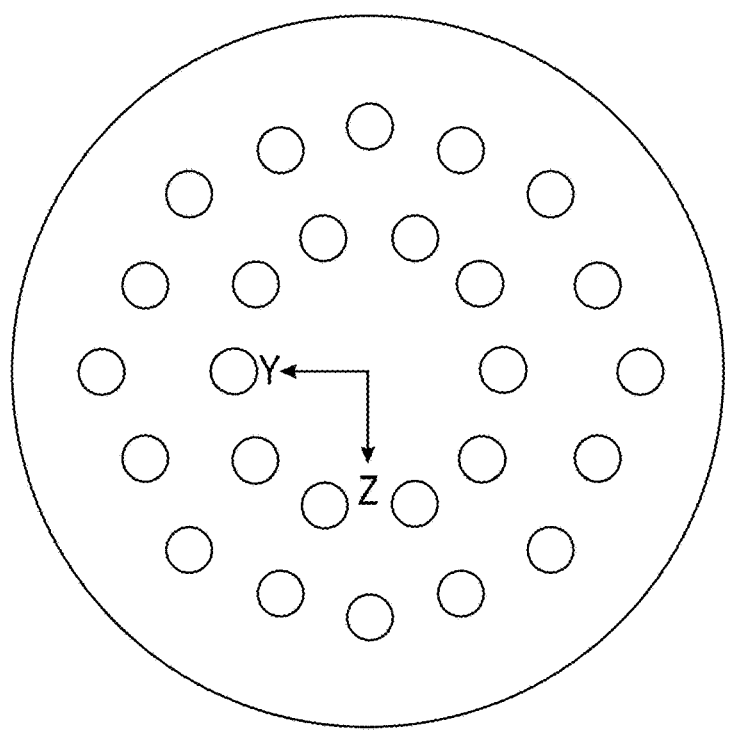

Here, femoral head and acetabular cup are considered to be made with Ti6Al4V and the liner material is taken as UHMWPE. Different body weights such as 600 N, 650 N, 700 N, 750 N, 800 N and 850 N are applied at the top of acetabular cup and the contact stress and sliding distance are determined for each load. Secondly, the nature of contact between femoral head and liner is changed. Metal on plastic type of contact between femoral head and liner is converted to plastic-on-plastic type of contact by attaching an additional liner material (UHMWPE) on the hemispherical surface of femoral head (Ti6Al4V) as shown in FIG. 6a. By this modification, direct contact of harder material on a softer material can be prevented (here the additional liner is fixed on the femoral head). The thickness of additional liner considered for the analysis are 1 mm, 2 mm and 3 mm. In all those cases the overall diameter of femoral head is kept as same. FIG. 6b depicts a cross sectional view of the femoral head provided with the additional liner, in accordance with the present invention.

Figure 8A:
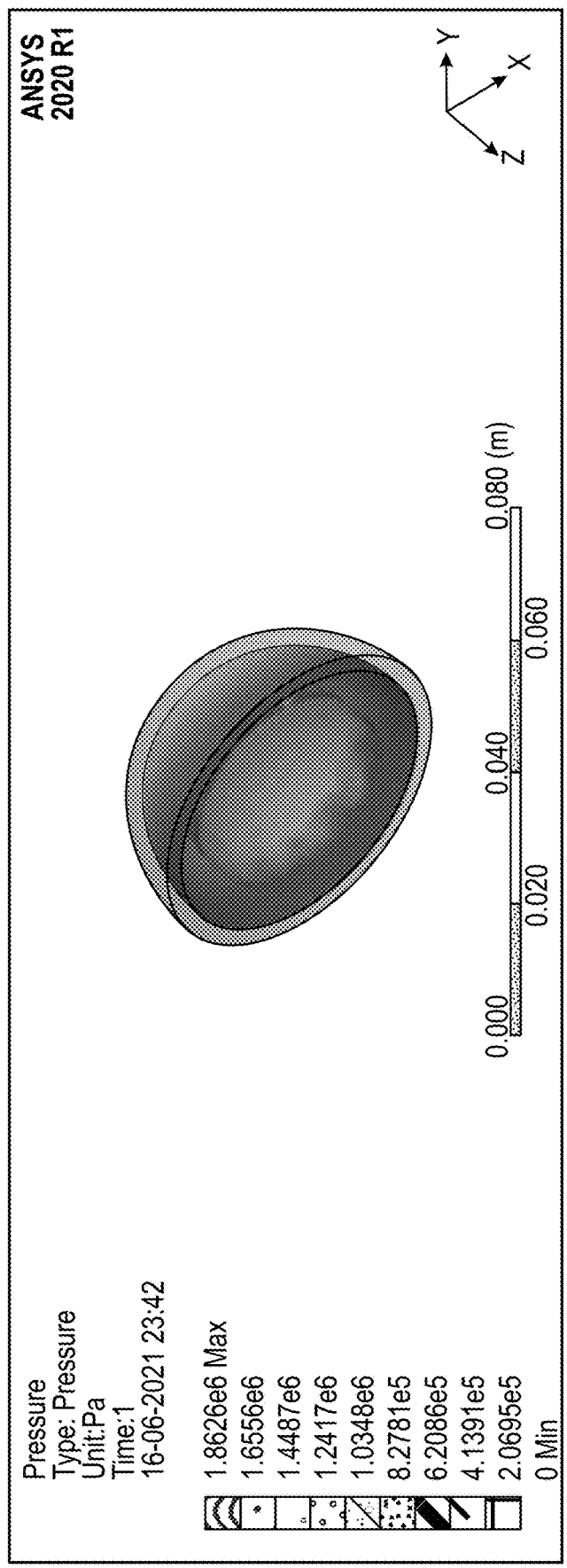
FIG. 8a and FIG. 8b show femoral heads with grooves of 1 mm, 2 mm, 3 mm, and 4 mm widths being numerically analyzed and the distribution of contact stress and sliding distance obtained for the femoral head with 1 mm wide groove, when subjected to 600 N force.
Figure 8B:
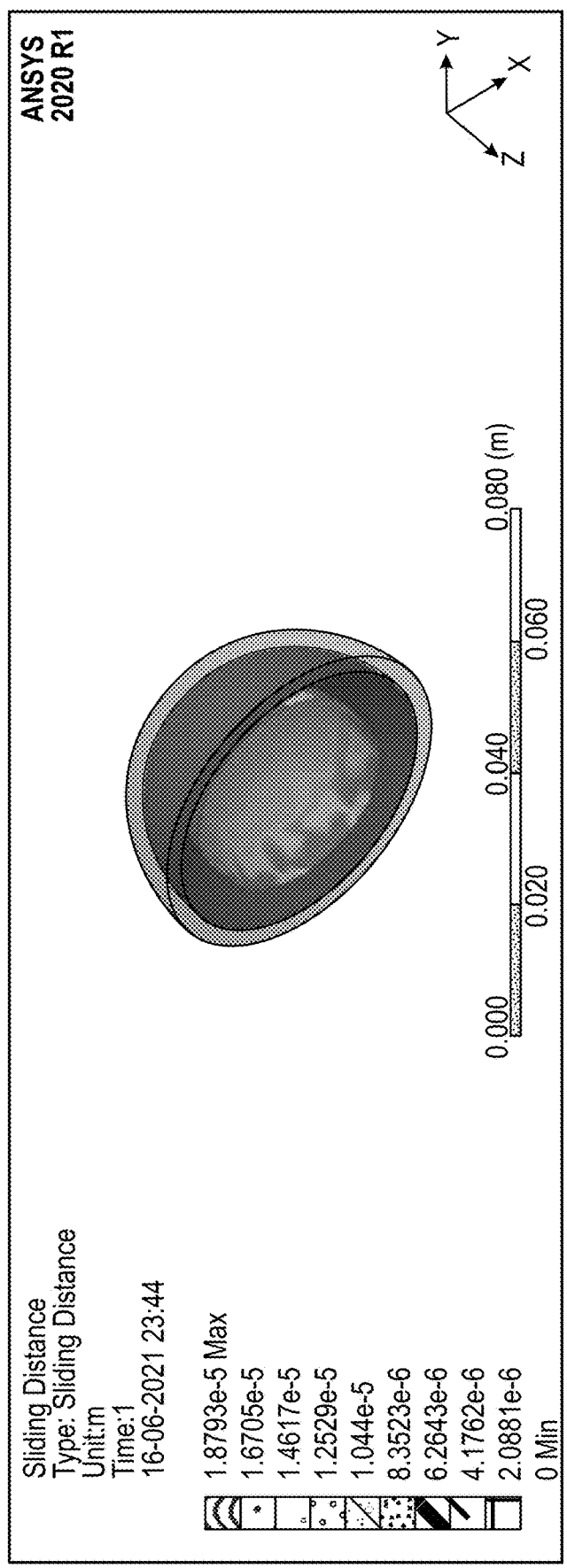

Finally, the effectiveness of textures of different shape and same surface area on the wear characteristics is analyzed. Here, surface area is fixed constant as 3.14 $mm^2$. Schematic diagrams of the textured surfaces considered in accordance with the present invention are given in FIG. 7a and FIG. 7b. The circular dimples are of 2 mm diameter and the edge length for square dimples is 1.57 mm Here, also the material combination used includes, the femoral head being made with titanium alloy (Ti6Al4V) and the liner being made with UHMWPE. Considering results obtained in accordance with the present invention from numerical models of surface modified and design modified femoral head under static loading condition, the wear volume per year for all these models are determined and the obtained results are compared with that obtained for a base model (a traditionally implemented model). The numerical simulation of these models are done to obtain the maximum value of contact pressure and sliding distance. The static loading condition is assumed to minimize complexity of the problem. Initially, femoral heads with grooves of 1 mm, 2 mm, 3 mm, and 4 mm widths are numerically analyzed and the distribution of contact stress and sliding distance obtained for the femoral head with 1 mm wide groove, when subjected to 600 N force, is shown in FIG. 8a and FIG. 8b. Here, the maximum value of contact pressure and sliding distance occurs at the central region and the minimum value occurs at circumferential region. The maximum values of contact stress and sliding distance obtained for the femoral head with 1 mm wide groove under different body weights is given in FIG. 9.

Contact stress and sliding distance are increasing linearly with increase in body weight. In all the analyzed cases, the maximum value is found at the central region of the femoral head. Table 4 shows the maximum value of contact pressure and sliding distance obtained for femoral head with grooves of different widths under different body weights. The width of grooves are changed to study its effect on the contact pressure and sliding distance. It is observed that the wear volume reduced up to 10% when grooves of 1 mm width are proved on the femoral head.

TABLE 4

Contact pressure and sliding distance for femoral head with grooves of different widths subjected to different loads

| Load (N) | Contact pressure (MPa) | | | | Sliding distance (mm) | | | |
|---|---|---|---|---|---|---|---|---|
| | 1 mm | 2 mm | 3 mm | 4 mm | 1 mm | 2 mm | 3 mm | 4 mm |
| 600 | 1.862 | 1.783 | 2.48 | 2.69 | 0.01879 | 0.0216 | 0.0209 | 0.021 |
| 650 | 1.926 | 1.868 | 2.59 | 2.81 | 0.0202 | 0.02z32 | 0.0226 | 0.0226 |
| 700 | 1.988 | 1.951 | 2.7025 | 2.946 | 0.021 | 0.0247 | 0.0242 | 0.0241 |
| 750 | 2.049 | 2.0338 | 2.810 | 3.0725 | 0.0230 | 0.0263 | 0.0258 | 0.0257 |

TABLE 4-continued

Contact pressure and sliding distance for femoral head with grooves of different widths subjected to different loads

| Load | Contact pressure (MPa) | | | | Sliding distance (mm) | | | |
|---|---|---|---|---|---|---|---|---|
| (N) | 1 mm | 2 mm | 3 mm | 4 mm | 1 mm | 2 mm | 3 mm | 4 mm |
| 800 | 2.06 | 2.122 | 2.919 | 3.197 | 0.0242 | 0.0278 | 0.0274 | 0.0272 |
| 850 | 2.16 | 2.2105 | 3.02 | 3.32 | 0.0259 | 0.0293 | 0.0289 | 0.0287 |

Figure 10A:
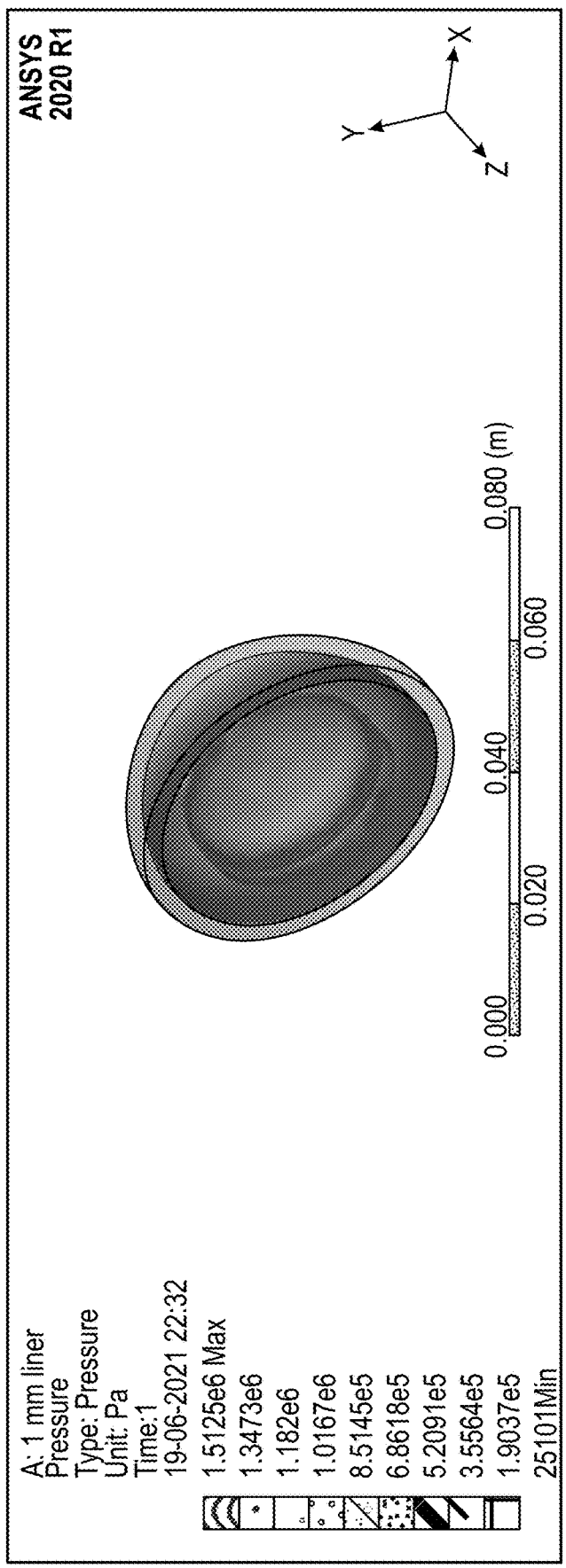
FIG. 10a and FIG. 10b depict the distribution of contact stress and sliding distance obtained for femoral head with additional liner of thickness 1 mm.
Figure 10B:
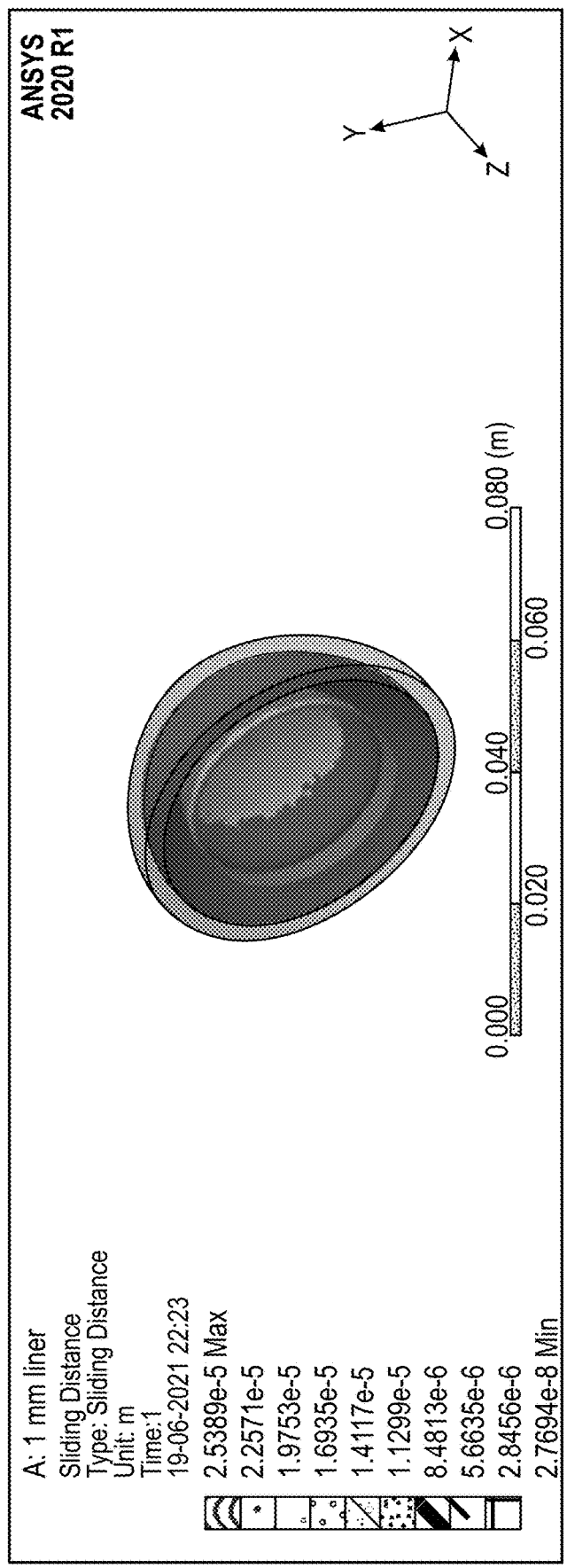

Secondly, an additional liner of UHMWPE is placed between femoral head and liner to avoid the direct contact of metal on plastic. Additional liners with thickness 1 mm, 2 mm and 3 mm are considered for the analysis. Better results compared to traditional methods are observed when an additional liner is incorporated as a design modification. The distribution of contact stress and sliding distance obtained for femoral head with additional liner of thickness 1 mm is shown in FIG. 10a and FIG. 10b. Here also the maximum value of contact pressure and sliding distance occurs at the central region and the minimum value occurs at circumferential region. The contact stress and sliding distance obtained for femoral head with additional liner of 1 mm thick, for different loads is given in FIG. 11.

Table 5 shows the complete data of contact pressure and sliding distance obtained for femoral head with additional liner of different thickness subjected to different loads. The contact pressure between femoral head surface and liner is less than that obtained in traditionally implemented methods for the same boundary conditions used. When the thickness of additional liner increases, the contact pressure also increases but which is less than that obtained by traditionally implemented methods.

TABLE 5

Contact pressure and sliding distance for femoral head with additional liner

| Load | Contact pressure (MPa) | | | Sliding distance (mm) | | |
|---|---|---|---|---|---|---|
| N | 1 mm | 2 mm | 3 mm | 1 mm | 2 mm | 3 mm |
| 600 | 1.5125 | 1.6903 | 1.9310 | 0.0253 | 0.0209 | 0.0169 |
| 650 | 1.5932 | 1.7816 | 2.0316 | 0.0274 | 0.0226 | 0.0185 |
| 700 | 1.6751 | 1.8700 | 2.1305 | 0.0294 | 0.0243 | 0.0199 |
| 750 | 1.7568 | 1.9576 | 2.2276 | 0.0314 | 0.0259 | 0.0214 |
| 800 | 1.8397 | 2.0439 | 2.3236 | 0.033 | 0.0275 | 0.0229 |
| 850 | 1.9229 | 2.1297 | 2.4173 | 0.0353 | 0.0292 | 0.0243 |

Finally circular and square dimples are made on the femoral head and a comparative analysis of contact stress and sliding distance is done. Table 6 shows the complete data of contact pressure and sliding distance obtained for femoral head with circular and square shaped dimples. It is observed that, the contact pressure and sliding distance obtained for square texture is higher than that of circular texture for all loads.

TABLE 6

Contact pressure and sliding distance for femoral head with circular and square shaped dimples

| | Circular hole | | Square hole | |
|---|---|---|---|---|
| Load (N) | Contact pressure (MPa) | Sliding distance (mm) | Contact pressure (MPa) | Siding distance (mm) |
| 600 | 3.3305 | 0.0106 | 4.335 | 0.01209 |
| 650 | 3.4289 | 0.0116 | 4.475 | 0.0133 |
| 700 | 3.5243 | 0.01258 | 4.483 | 0.01447 |
| 750 | 3.618 | 0.01352 | 4.687 | 0.01562 |
| 800 | 3.7107 | 0.01446 | 4.788 | 0.0167 |
| 850 | 3.8005 | 0.0154 | 4.887 | 0.0178 |

Figure 12:
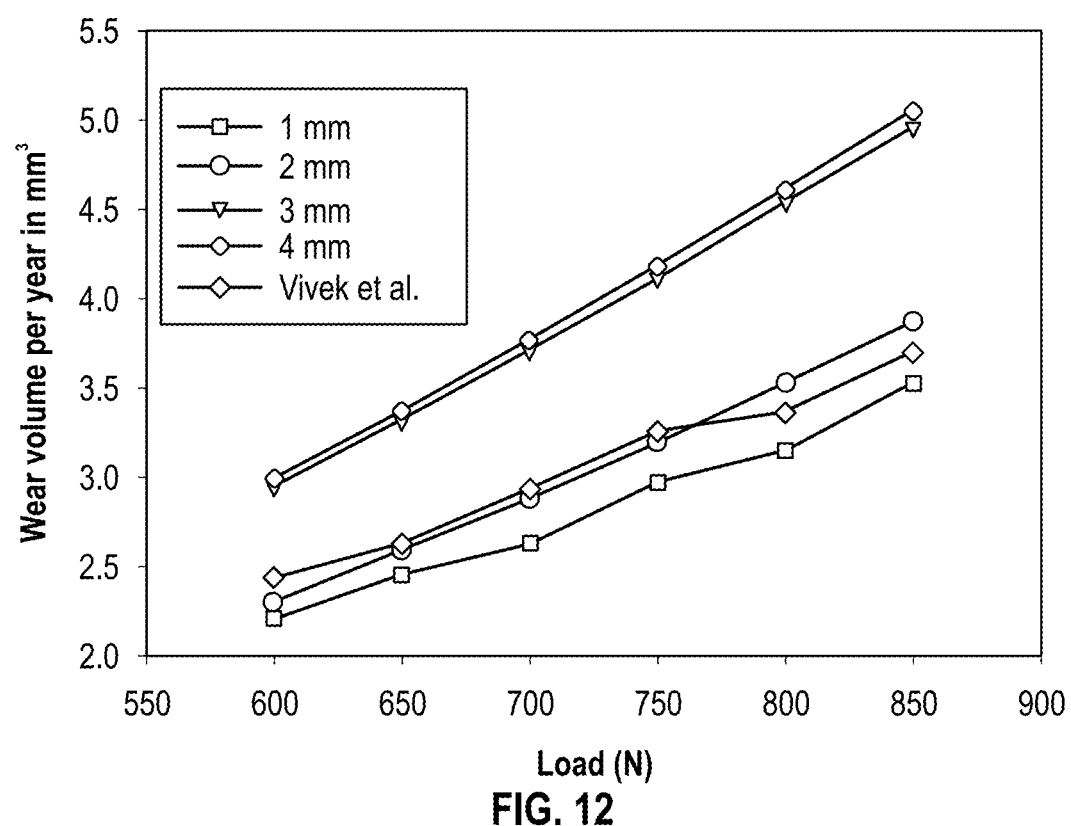
FIG. 12 depicts the variation in wear volume for femoral heads with grooves of different width subjected to different loads.

In an embodiment of the present invention, wear volume is determined for both the surface modified and design modified femoral heads using modified Archard's wear law. Modified Archard's equation is mentioned in equation 2. The contact pressure and sliding distance obtained from numerical analysis is used in the Archard's wear equation for the determination of wear volume. In the case of surface modification by providing semicircular grooves, wear volume varies with groove size based on modified Archard's law. Even though the area of contact is reducing in each case, wear volume is increasing with increase in contact pressure and sliding distance. FIG. 12 depicts the variation in wear volume for femoral heads with grooves of different width subjected to different loads. The graph also compares the wear volume obtained by traditional methods for the same material combination used. The results demonstrate that in the stand-up state for different body weight condition, femoral head with 4 mm wide groove succumbed the maximum wear. It is inferred that the wear volume of artificial hip joint implants decreases with increase in groove size.

Figure 13:
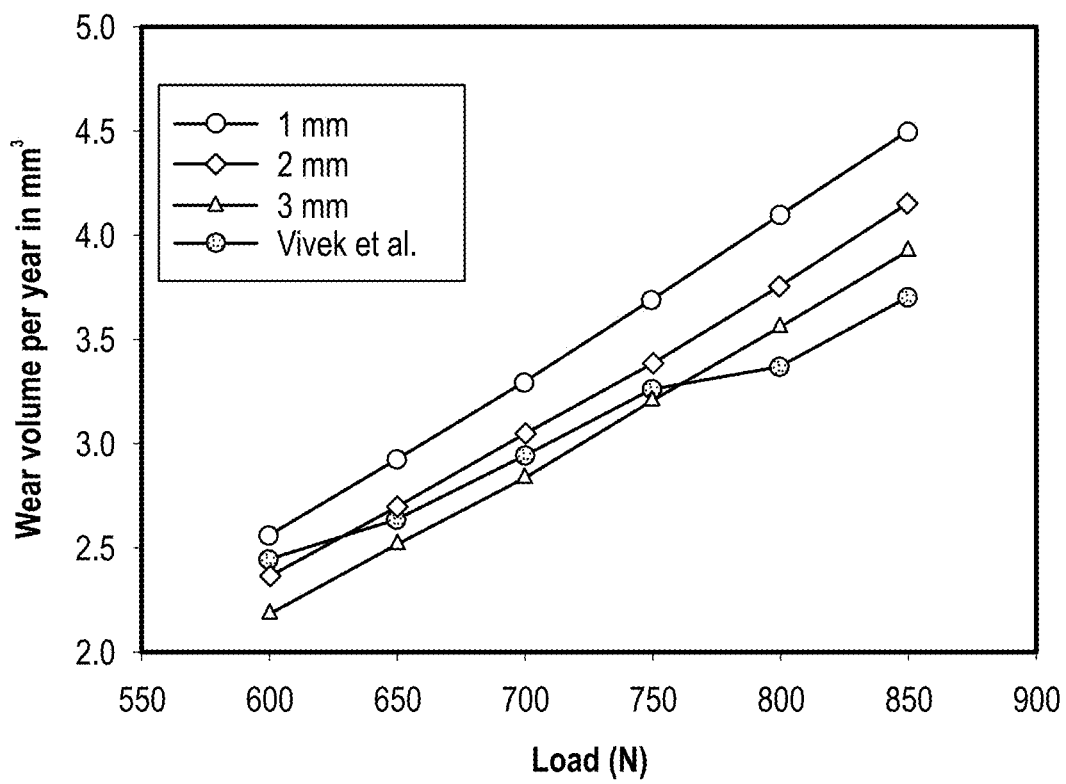
FIG. 13 depicts the variation in wear volume for femoral heads with additional liners of different thickness subjected to different loads.
Figure 14:
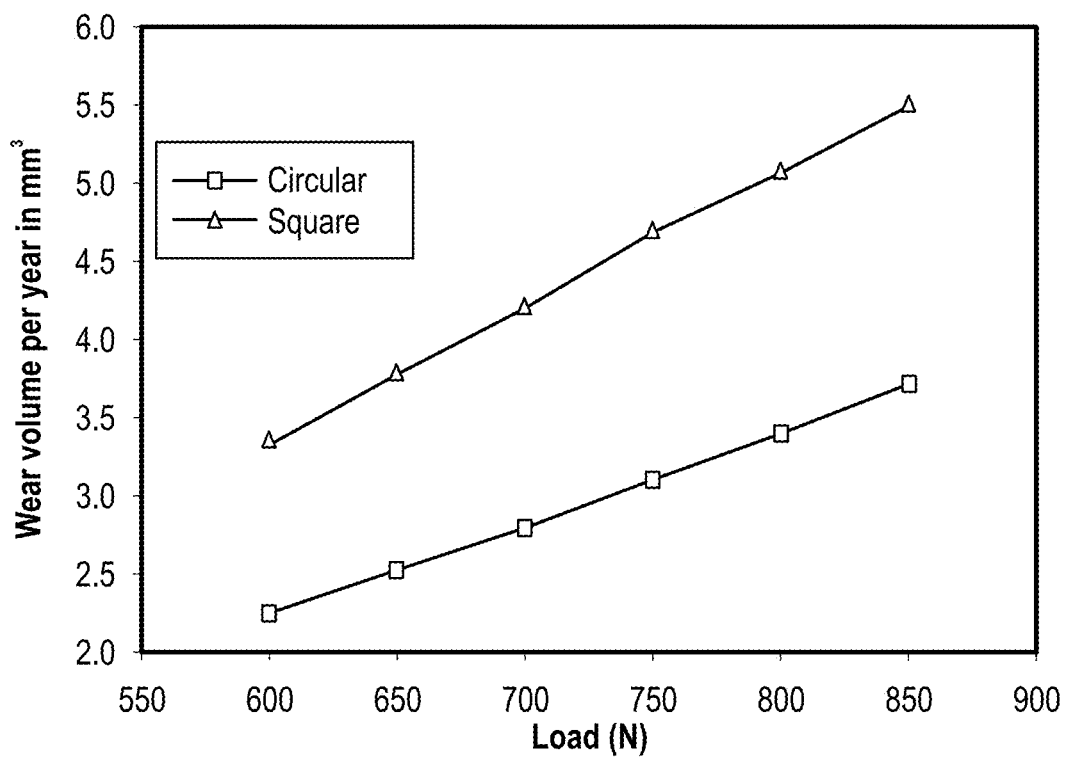
FIG. 14 graphically depicts the variation of wear volume with body weight for femoral heads with circular and square shaped textures.

The modification of the femoral head by the incorporation of an additional liner demonstrates that there is no considerable reduction of wear volume when an additional liner is attached on the femoral head surface. It is getting decreased when additional liner thickness is increasing. FIG. 13 depicts the variation in wear volume for femoral heads with additional liners of different thickness subjected to different loads. The graph also gives a comparison of the results of wear volume obtained by traditional methods for the same material combination used. The results demonstrate that in the stand-up state for different body weight condition, the wear mostly occurs in 1 mm thick additional liner. When the femoral head was attached with additional liner of 3 mm, the wear volume has the lowest value, and hence it is inferred that the wear volume of femoral head region of implant is getting reduced when the thickness of additional liner is increased. The wear volume per year is minimum for circular dimples and it increases linearly with body weight as shown in FIG. 14. Finite element analysis is conducted on design modified and surface modified femoral head for the estimation of wear volume per year based on the well-known modified Archard's wear law and results are compared with that in literature.

In accordance with the present invention, the wear behavior not only depends on the material properties but also on the contact surface area between femoral head and acetabular cup. Also, not much reduction in wear volume is observed with the provision of an additional liner between femoral head and liner. Grooves on the femoral head helps to reduce the wear volume, and also entraps the debris produced by liner material and thus reduces the adhesive wear. Femoral head with circular dimples yielded less wear volume than femoral head with square dimples, and modification of femoral head reduces the contact pressure which in turn reduces chance of implant failure.

Accordingly, based on various numerical studies conducted in accordance with the present invention, it is evidential that the proposed implant is able to solve major wear problems. The design modification is implemented by providing grooves on the femoral head and surface modification by providing macro sized dimples on femoral head, which has not been implemented till now. This idea reduces the chance of formation of abrasive wear produced by tiny implant particles by entrapping inside the modifications. Previously implemented designs have included providing an additional liner between the femoral head and liner, however in accordance with the present invention, an inner liner is attached on the femoral head, and the liner is additionally fixed to the femoral head at a certain thickness (1 mm, 2 mm, 3 mm) and by maintaining a constant overall spherical femoral head diameter of 32 mm.

Summarizing the overall effects of the proposed design, contact pressure, sliding distance and area of contact is changed as a result of the implemented modifications. These parameters are applied in Archard's wear equation and accordingly identified that the wear rate is reduced up to 10% by surface modification and 3% by design modifications in comparison with traditional implants. Wear rate is reduced and chances of inflammation due to the wear debris is also reduced, and moreover life of implant is increased. The wide-spread demand for implants is increasing day by day, and wear is one of the major problems that affects the performance of existing hip implants. The present invention is focused on reducing wear characteristics by surface and design modification of the femoral head and thereby developing a new hip implant. The proposed implant design has the ability to become an implant with lesser wear characteristics and better comfort for patients.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A hip implant structure, comprising:
   a stem and a femoral head, the femoral head comprising a plurality of grooves, and
   an acetabular cup and an inner liner,
   wherein presence of the inner liner and plurality of grooves on the femoral head reduces friction thereby reducing wear of the hip implant structure, the inner liner being fixed within the acetabular cup, and
   wherein an additional or second liner is further attached on a hemispherical surface of the femoral head by maintaining a constant spherical femoral head diameter, converting the contact between the femoral head and the inner liner from a metal-on-plastic contact to a plastic-on-plastic contact.

2. The hip implant structure of claim 1, wherein the hip implant structure is used for total hip arthroplasty.

3. The hip implant structure of claim 1, wherein the femoral head is hemi-spherical in structure.

4. The hip implant structure of claim 1, wherein the femoral head is made of titanium alloy (Ti6Al4V).

5. The hip implant structure of claim 1, wherein the inner liner is made of ultra-high molecular weight polyethylene (UHMWPE).

6. The hip implant structure of claim 1, wherein an inner radius of the inner liner is 16 mm and an outer radius of the inner liner is 23 mm.

7. The hip implant structure of claim 1, wherein the additional or second liner attached on the hemispherical surface of the femoral head is made of ultra-high molecular weight polyethylene (UHMWPE).

8. The hip implant structure of claim 1, wherein a thickness of the additional or second liner is 1 mm, 2 mm, or 3 mm while maintaining a constant overall spherical femoral head diameter of 32 mm.

9. The hip implant structure of claim 1, wherein the plurality of grooves on the femoral head comprises a plurality of hemispherical grooves of varying widths.

10. The hip implant structure of claim 1, wherein debris produced by the inner liner gets trapped inside the plurality of grooves, resulting in a reduced chance of adhesive wear.

11. The hip implant structure of claim 1, wherein a surface of the femoral head is textured.

12. The hip implant structure of claim 11, wherein the surface of the femoral head comprises a plurality of circular and square shaped dimples, wear volume per year being minimum for the circular shaped dimples.

13. The hip implant structure of claim 12, wherein the diameter of the circular dimples is 2 mm.

* * * * *